United States Patent
Dillon et al.

(10) Patent No.: US 8,016,851 B2
(45) Date of Patent: Sep. 13, 2011

(54) DELIVERY SYSTEM AND METHOD OF DELIVERY FOR TREATING OBESITY

(75) Inventors: Travis E. Dillon, Winston-Salem, NC (US); Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 780 days.

(21) Appl. No.: 11/965,531

(22) Filed: Dec. 27, 2007

(65) Prior Publication Data
US 2009/0171382 A1 Jul. 2, 2009

(51) Int. Cl.
*A61M 29/00* (2006.01)
(52) U.S. Cl. ..................... 606/192; 623/23.65
(58) Field of Classification Search .......... 606/191–196, 606/198; 623/23.64–23.68; 604/101.02, 604/101.03, 103.07, 104, 907, 909–910, 604/916–920; 600/207
See application file for complete search history.

(56) References Cited

U.S. PATENT DOCUMENTS

| | | | |
|---|---|---|---|
| 2,508,690 A | | 5/1950 | Schmerl |
| 4,133,315 A * | | 1/1979 | Berman et al. ................ 606/193 |
| 4,134,405 A | | 1/1979 | Smit |
| 4,246,893 A | | 1/1981 | Berson |
| 4,315,509 A | | 2/1982 | Smit |
| 4,403,604 A | | 9/1983 | Wilkinson et al. |
| 4,416,267 A * | | 11/1983 | Garren et al. ................ 128/898 |
| 4,447,227 A * | | 5/1984 | Kotsanis .................... 604/95.03 |
| 4,485,805 A * | | 12/1984 | Foster, Jr. ..................... 128/898 |
| 4,512,338 A * | | 4/1985 | Balko et al. ................... 606/108 |
| 4,558,699 A | | 12/1985 | Bashour |
| 4,607,618 A | | 8/1986 | Angelchik |
| 4,694,827 A * | | 9/1987 | Weiner et al. ................ 606/192 |
| 4,696,288 A | | 9/1987 | Kuzmak et al. |
| 4,723,547 A | | 2/1988 | Kullas et al. |
| 4,803,985 A | | 2/1989 | Hill |
| 4,878,905 A | | 11/1989 | Blass |
| 4,899,747 A | | 2/1990 | Garren et al. |
| 4,925,446 A | | 5/1990 | Garay et al. |
| 4,952,339 A | | 8/1990 | Temus et al. |
| 4,983,167 A * | | 1/1991 | Sahota .......................... 606/194 |

(Continued)

FOREIGN PATENT DOCUMENTS

EP 0137 878 11/1983

(Continued)

OTHER PUBLICATIONS

English Language Translation of WO2007/012443 A1.*

(Continued)

*Primary Examiner* — Gary Jackson
*Assistant Examiner* — Erin Colello
(74) *Attorney, Agent, or Firm* — Brinks Hofer Gilson & Lione

(57) ABSTRACT

A delivery system and method of use thereof for introducing a bundled intragastric bag into a gastric lumen are described. The delivery system includes a pushing mechanism movable between an unexpanded and expanded configuration. The pushing mechanism in its expanded configuration pushes each of the bundles of the bag into the gastric lumen. A suture strand is periodically pulled during the procedure to help create doughnut-shaped bundles. Another suture strand extends between a proximal button and distal button of the deployed assembly to maintain the doughnut-shaped bundle structure.

21 Claims, 7 Drawing Sheets

U.S. PATENT DOCUMENTS

| | | | |
|---|---|---|---|
| 5,129,915 A | 7/1992 | Cantenys | |
| 5,234,454 A | 8/1993 | Bangs | |
| 5,246,456 A | 9/1993 | Wilkinson | |
| 5,265,622 A * | 11/1993 | Barbere | 600/585 |
| 5,306,300 A | 4/1994 | Berry | |
| 5,327,914 A | 7/1994 | Shlain | |
| 5,345,949 A | 9/1994 | Shlain | |
| 5,507,769 A * | 4/1996 | Marin et al. | 606/198 |
| 5,520,609 A * | 5/1996 | Moll et al. | 600/204 |
| 5,547,458 A * | 8/1996 | Ortiz et al. | 600/204 |
| 5,766,203 A * | 6/1998 | Imran et al. | 623/1.11 |
| 5,779,688 A * | 7/1998 | Imran et al. | 604/533 |
| 5,827,304 A * | 10/1998 | Hart | 606/159 |
| 5,868,141 A | 2/1999 | Ellias | |
| 5,938,669 A | 8/1999 | Klaiber et al. | |
| 5,976,106 A * | 11/1999 | Verin et al. | 604/103.07 |
| 5,985,307 A * | 11/1999 | Hanson et al. | 424/423 |
| 5,993,473 A | 11/1999 | Chan et al. | |
| 6,067,991 A | 5/2000 | Forsell | |
| 6,210,347 B1 | 4/2001 | Forsell | |
| 6,427,089 B1 | 7/2002 | Knowlton | |
| 6,450,946 B1 | 9/2002 | Forsell | |
| 6,454,699 B1 | 9/2002 | Forsell | |
| 6,460,543 B1 | 10/2002 | Forsell | |
| 6,511,490 B2 | 1/2003 | Robert | |
| 6,540,789 B1 | 4/2003 | Silverman et al. | |
| 6,558,400 B2 | 5/2003 | Deem et al. | |
| 6,616,678 B2 * | 9/2003 | Nishtala et al. | 606/198 |
| 6,627,206 B2 | 9/2003 | Lloyd | |
| 6,656,194 B1 | 12/2003 | Gannoe et al. | |
| 6,675,809 B2 | 1/2004 | Stack et al. | |
| 6,676,674 B1 | 1/2004 | Dudai | |
| 6,733,512 B2 | 5/2004 | McGhan | |
| 6,740,121 B2 | 5/2004 | Geitz | |
| 6,746,460 B2 | 6/2004 | Gannoe et al. | |
| 6,755,869 B2 | 6/2004 | Geitz | |
| 6,802,868 B2 | 10/2004 | Silverman et al. | |
| 6,845,776 B2 | 1/2005 | Stack et al. | |
| 6,879,859 B1 | 4/2005 | Boveja | |
| 6,916,326 B2 | 7/2005 | Benchetrit | |
| 6,946,002 B2 | 9/2005 | Geitz | |
| 6,981,980 B2 | 1/2006 | Sampson et al. | |
| 6,994,715 B2 | 2/2006 | Gannoe et al. | |
| 7,033,373 B2 | 4/2006 | de la Torre et al. | |
| 7,033,384 B2 | 4/2006 | Gannoe et al. | |
| 7,037,344 B2 | 5/2006 | Kagan et al. | |
| 7,054,690 B2 | 5/2006 | Imran | |
| 7,056,305 B2 | 6/2006 | Garza Alvarez | |
| 7,066,945 B2 | 6/2006 | Hashiba et al. | |
| 7,090,688 B2 * | 8/2006 | Nishtala et al. | 606/198 |
| 7,090,699 B2 | 8/2006 | Geitz | |
| 7,097,665 B2 * | 8/2006 | Stack et al. | 623/23.65 |
| 7,112,186 B2 | 9/2006 | Shah | |
| 7,121,283 B2 | 10/2006 | Stack et al. | |
| 7,152,607 B2 | 12/2006 | Stack et al. | |
| 7,172,613 B2 | 2/2007 | Wazne | |
| 7,175,638 B2 | 2/2007 | Gannoe et al. | |
| 7,177,693 B2 | 2/2007 | Starkebaum | |
| 7,335,210 B2 * | 2/2008 | Smit | 606/108 |
| 7,753,928 B2 * | 7/2010 | de la Torre et al. | 606/191 |
| 2001/0011543 A1 | 8/2001 | Forsell | |
| 2001/0020150 A1 * | 9/2001 | Ravo | 604/101.01 |
| 2002/0055757 A1 * | 5/2002 | Torre et al. | 606/192 |
| 2002/0188354 A1 | 12/2002 | Peghini | |
| 2003/0049325 A1 | 3/2003 | Suwelack et al. | |
| 2003/0078611 A1 * | 4/2003 | Hashiba et al. | 606/191 |
| 2003/0109892 A1 | 6/2003 | Deem et al. | |
| 2003/0120265 A1 | 6/2003 | Deem et al. | |
| 2003/0158564 A1 | 8/2003 | Benchetrit | |
| 2003/0199989 A1 | 10/2003 | Stack et al. | |
| 2003/0199990 A1 | 10/2003 | Stack et al. | |
| 2003/0199991 A1 | 10/2003 | Stack et al. | |
| 2004/0019388 A1 | 1/2004 | Starkebaum | |
| 2004/0024386 A1 | 2/2004 | Deem et al. | |
| 2004/0039452 A1 | 2/2004 | Bessler | |
| 2004/0044353 A1 | 3/2004 | Gannoe | |
| 2004/0044354 A1 | 3/2004 | Gannoe et al. | |
| 2004/0049209 A1 | 3/2004 | Benchetrit | |
| 2004/0082963 A1 | 4/2004 | Gannoe et al. | |
| 2004/0092892 A1 * | 5/2004 | Kagan et al. | 604/264 |
| 2004/0092974 A1 | 5/2004 | Gannoe et al. | |
| 2004/0117031 A1 | 6/2004 | Stack et al. | |
| 2004/0122452 A1 | 6/2004 | Deem et al. | |
| 2004/0122453 A1 | 6/2004 | Deem et al. | |
| 2004/0122526 A1 | 6/2004 | Imran | |
| 2004/0138760 A1 | 7/2004 | Schurr | |
| 2004/0138761 A1 | 7/2004 | Stack et al. | |
| 2004/0143342 A1 | 7/2004 | Stack et al. | |
| 2004/0153106 A1 | 8/2004 | Dudai | |
| 2004/0158331 A1 | 8/2004 | Stack et al. | |
| 2004/0167625 A1 * | 8/2004 | Beyar et al. | 623/11.11 |
| 2004/0172141 A1 | 9/2004 | Stack | |
| 2004/0186503 A1 | 9/2004 | DeLegge | |
| 2004/0220682 A1 | 11/2004 | Levine et al. | |
| 2004/0243152 A1 | 12/2004 | Taylor et al. | |
| 2005/0049718 A1 | 3/2005 | Dann et al. | |
| 2005/0096750 A1 | 5/2005 | Kagan et al. | |
| 2005/0131500 A1 * | 6/2005 | Zalesky et al. | 607/89 |
| 2005/0149141 A1 | 7/2005 | Starkebaum | |
| 2005/0149142 A1 | 7/2005 | Starkebaum | |
| 2005/0177181 A1 | 8/2005 | Kagan et al. | |
| 2005/0192531 A1 | 9/2005 | Birk | |
| 2005/0192614 A1 | 9/2005 | Binmoeller | |
| 2005/0209653 A1 | 9/2005 | Herbert et al. | |
| 2005/0222637 A1 | 10/2005 | Chen | |
| 2005/0222638 A1 | 10/2005 | Foley et al. | |
| 2005/0240239 A1 | 10/2005 | Bojeva et al. | |
| 2005/0240279 A1 | 10/2005 | Kagan et al. | |
| 2005/0245957 A1 | 11/2005 | Starkebaum et al. | |
| 2005/0246037 A1 | 11/2005 | Starkebaum | |
| 2005/0250979 A1 | 11/2005 | Coe | |
| 2005/0256587 A1 | 11/2005 | Egan | |
| 2005/0267405 A1 | 12/2005 | Shah | |
| 2005/0267596 A1 * | 12/2005 | Chen et al. | 623/23.67 |
| 2005/0277975 A1 * | 12/2005 | Saadat et al. | 606/191 |
| 2006/0015151 A1 | 1/2006 | Aldrich | |
| 2006/0020247 A1 | 1/2006 | Kagan et al. | |
| 2006/0030949 A1 | 2/2006 | Geitz | |
| 2006/0058923 A1 * | 3/2006 | Lesh et al. | 623/23.72 |
| 2006/0074450 A1 | 4/2006 | Boveja et al. | |
| 2006/0079944 A1 | 4/2006 | Imran | |
| 2006/0089571 A1 | 4/2006 | Gertner | |
| 2006/0129027 A1 | 6/2006 | Catona | |
| 2006/0129094 A1 | 6/2006 | Shah | |
| 2006/0161172 A1 | 7/2006 | Levine et al. | |
| 2006/0206063 A1 | 9/2006 | Kagan et al. | |
| 2006/0206064 A1 | 9/2006 | Kagan et al. | |
| 2006/0206160 A1 | 9/2006 | Cigaina et al. | |
| 2006/0249165 A1 | 11/2006 | Silverman et al. | |
| 2006/0253142 A1 | 11/2006 | Bjerken | |
| 2006/0257444 A1 | 11/2006 | Tropsha et al. | |
| 2006/0257445 A1 | 11/2006 | Tropsha et al. | |
| 2006/0257446 A1 | 11/2006 | Tropsha et al. | |
| 2006/0282107 A1 * | 12/2006 | Hashiba et al. | 606/153 |
| 2006/0293742 A1 | 12/2006 | Dann et al. | |
| 2007/0004963 A1 | 1/2007 | Benchetrit | |
| 2007/0010794 A1 | 1/2007 | Dann et al. | |
| 2007/0010864 A1 | 1/2007 | Dann et al. | |
| 2007/0010865 A1 | 1/2007 | Dann et al. | |
| 2007/0010866 A1 | 1/2007 | Dann et al. | |
| 2007/0021761 A1 | 1/2007 | Phillips | |
| 2007/0038308 A1 | 2/2007 | Geitz | |
| 2007/0078476 A1 * | 4/2007 | Hull et al. | 606/191 |
| 2007/0083224 A1 * | 4/2007 | Hively | 606/192 |
| 2007/0100368 A1 * | 5/2007 | Quijano et al. | 606/192 |
| 2007/0100369 A1 * | 5/2007 | Cragg et al. | 606/192 |
| 2007/0239284 A1 * | 10/2007 | Skerven et al. | 623/23.65 |
| 2008/0109027 A1 * | 5/2008 | Chen et al. | 606/191 |
| 2009/0105641 A1 * | 4/2009 | Nissl | 604/97.02 |

FOREIGN PATENT DOCUMENTS

| | | | |
|---|---|---|---|
| WO | WO 2004/019765 A | 3/2004 | |
| WO | WO 2006122019 A2 * | 11/2006 | |
| WO | WO 2007/018122 A | 2/2007 | |
| WO | WO 2007012443 A1 * | 2/2007 | |

OTHER PUBLICATIONS

PCT International Search Report for PCT/US2008/086975, filed Dec. 16, 2008.

PCT Written Opinion for PCT/US2008/086975, filed Dec. 16, 2008.

* cited by examiner

DELIVERY SYSTEM AND METHOD OF DELIVERY FOR TREATING OBESITY

TECHNICAL FIELD

This invention relates to medical devices, and more particularly to obesity treatment devices that can be placed in the stomach of a patient to reduce the size of the stomach reservoir or to place pressure on the inside surface of the stomach.

BACKGROUND OF THE INVENTION

It is well known that obesity is a very difficult condition to treat. Methods of treatment are varied, and include drugs, behavior therapy, and physical exercise, or often a combinational approach involving two or more of these methods. Unfortunately, results are seldom long term, with many patients eventually returning to their original weight over time. For that reason, obesity, particularly morbid obesity, is often considered an incurable condition. More invasive approaches have been available which have yielded good results in many patients. These include surgical options such as bypass operations or gastroplasty. However, these procedures carry high risks and are therefore not appropriate for most patients.

In the early 1980s, physicians began to experiment with the placement of intragastric balloons to reduce the size of the stomach reservoir, and consequently its capacity for food. Once deployed in the stomach, the balloon helps to trigger a sensation of fullness and a decreased feeling of hunger. These balloons are typically cylindrical or pear-shaped, generally range in size from 200-500 ml or more, are made of an elastomer such as silicone, polyurethane, or latex, and are filled with air, water, or saline. While some studies demonstrated modest weight loss, the effects of these balloons often diminished after three or four weeks, possibly due to the gradual distension of the stomach or the fact that the body adjusted to the presence of the balloon. Other balloons include a tube exiting the nasal passage that allows the balloon to be periodically deflated and re-insufflated to better simulate normal food intake. However, the disadvantages of having an inflation tube exiting the nose are obvious.

The experience with balloons as a method of treating obesity has provided uncertain results, and has been frequently disappointing. Some trials failed to show significant weight loss over a placebo, or were ineffective unless the balloon placement procedure was combined with a low-calorie diet. Complications have also been observed, such as gastric ulcers, especially with use of fluid-filled balloons, and small bowel obstructions caused by deflated balloons. In addition, there have been documented instances of the balloon blocking off or lodging in the opening to the duodenum, wherein the balloon may act like a ball valve to prevent the stomach contents from emptying into the intestines.

Unrelated to the above-discussed methods for treating obesity, it has been observed that the ingestion of certain indigestible matter, such as fibers, hair, fuzzy materials, etc., can collect in the stomach over time, and eventually form a mass called a bezoar. In some patients, particularly children and the mentally handicapped, bezoars often result from the ingestion of plastic or synthetic materials. In many cases, bezoars can cause indigestion, stomach upset, or vomiting, especially if allowed to grow sufficiently large. It has also been documented that certain individuals having bezoars are subject to weight loss, presumably due to the decrease in the size of the stomach reservoir. Although bezoars may be removed endoscopically, especially in conjunction with a device known as a bezotome or bezotriptor, they, particularly larger ones, often require surgery.

What is needed is an intragastric device that provides the potential weight loss benefits of a bezoar or intragastric balloon without the associated complications. Ideally, such a device should be well-tolerated by the patient, effective over a long period of time, sizable for individual anatomies, and easy to place and retrieve.

SUMMARY OF THE INVENTION

In one aspect of the invention, a delivery system for introducing an obesity device into a gastric lumen is provided. An overtube including a proximal end and a distal end is provided. An inner member having a first distal end is provided. An outer member including a second distal end is also provided. The outer member is slidably disposed over the inner member. The outer member comprises a pushing mechanism disposed at the second distal end. The pushing mechanism is moveable between a expanded configuration and an unexpanded configuration. The pushing mechanism in the expanded configuration is adapted to push an incremental length of the obesity device into the gastric lumen.

In a second aspect of the invention, a method for introducing an intragastric bag into a gastric lumen is provided. The method comprises the steps of providing a delivery system. The system includes an overtube having a proximal end and a distal end, an inner member having a first distal end, and an outer member including a second distal end. The outer member is slidably disposed over the inner member. The outer member comprises a pushing mechanism disposed at the second distal end. The pushing mechanism is moveable between a expanded configuration and an unexpanded configuration, wherein the pushing mechanism in the expanded configuration spans a distance sufficient to push an incremental length of the bag into the gastric lumen. The intragastric bag is partitioned into a plurality of bundles with a plurality of retaining elements, the plurality of retaining elements being disposed circumferentially about the plurality of bundles, and the plurality of retaining elements being spaced apart a predetermined distance from each other. The bundled intragastric bag is then loaded over the outer member. The outer member is proximally pulled through a first retaining element with the pushing mechanism configured in the unexpanded configuration and positioned in the bag proximal and adjacent to the first retaining element. The pushing mechanism is then expanded. Flaring of the pushing mechanism causes the outer member to move in a distal direction so as to push the first retaining element from the plurality of retaining elements and a first bundle of the plurality of bundles into the gastric lumen.

In a third aspect of the invention, an intragastric bag for the treatment of obesity is provided. The intragastric bag comprises a digestive-resistant material in a configuration sufficiently large to prevent the intragastric bag from passing through a mammal's pylorus, wherein the intragastric bag is configured to function as an artificial bezoar, and further wherein the bag comprises a plurality of doughnut-shaped bundles, each of the plurality of doughnut-shaped bundles having atramautic rounded edges.

BRIEF DESCRIPTION OF SEVERAL VIEWS OF THE DRAWINGS

Several embodiments of the present invention will now be described by way of example with reference to the accompanying drawings, in which.

DETAILED DESCRIPTION OF THE INVENTION

Figure 1:
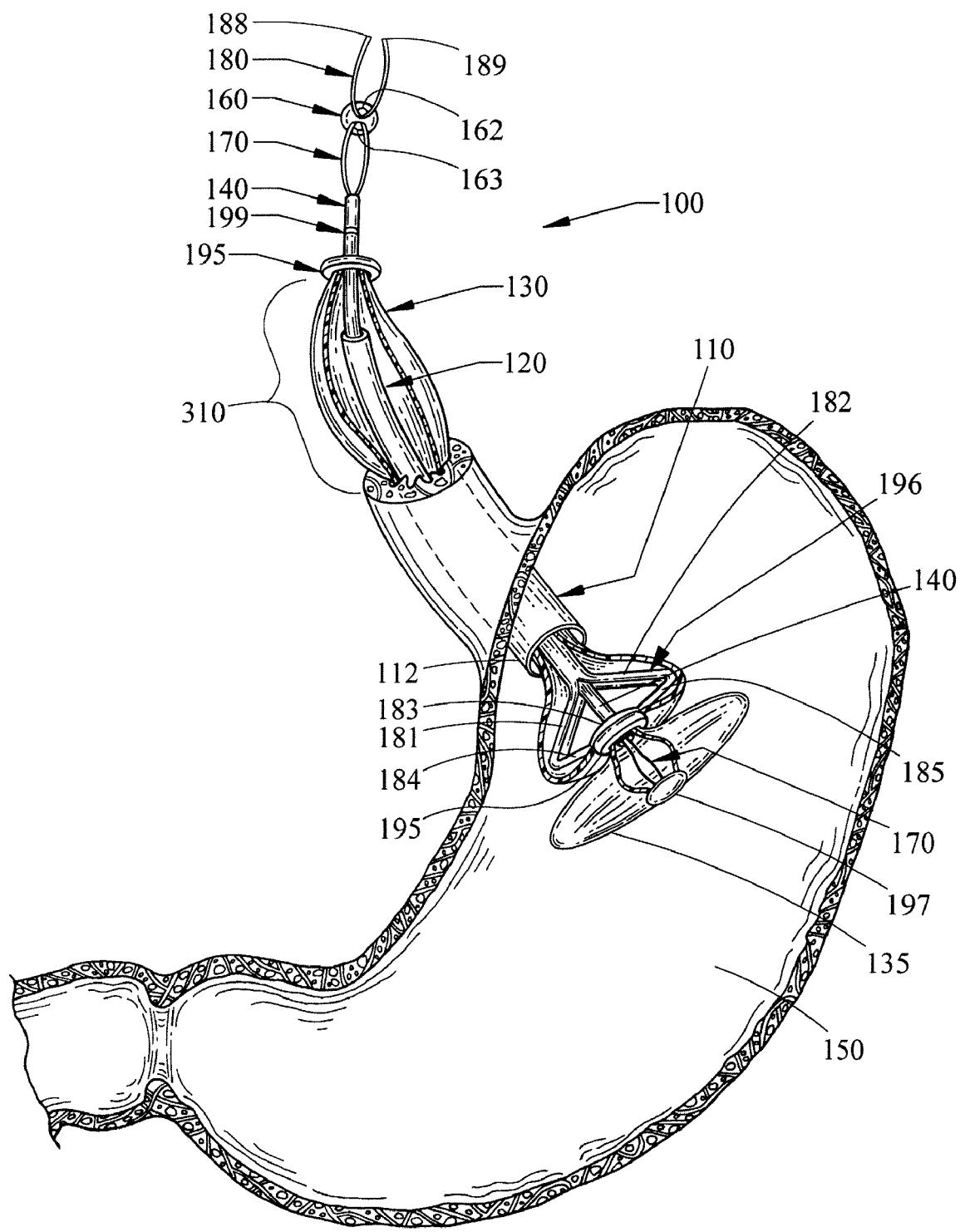
FIG. 1 shows a delivery system deploying a first bundle of an intragastric bag into a gastric lumen.
Figure 6:
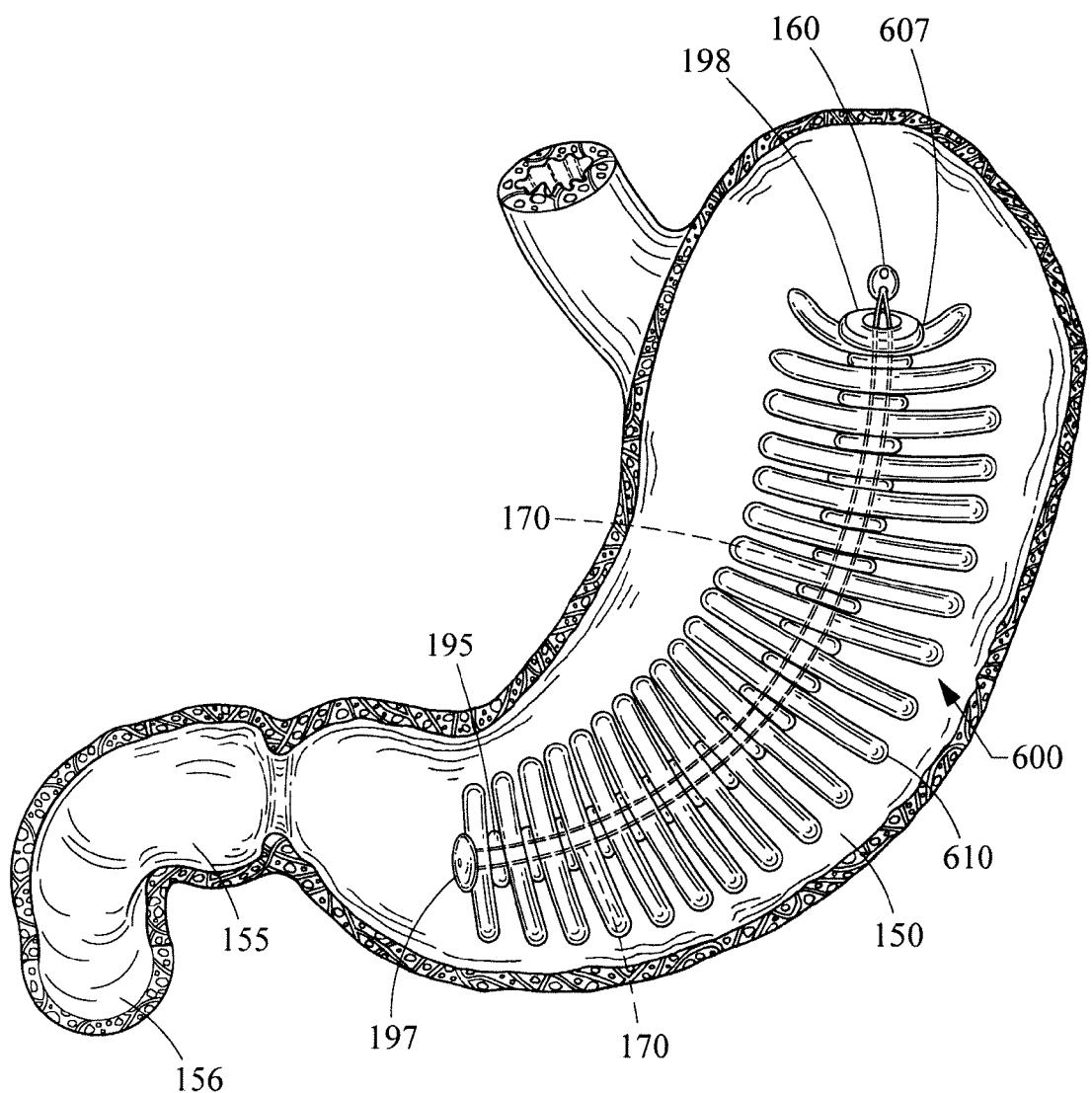
FIG. 6 shows the final implanted intragastric bag within the gastric lumen, the bundles of the intragastric being secured by a distal button and a proximal button snapped into a suture bead.

FIG. 1 depicts an embodiment of an exemplary delivery system 100 for delivering an intragastric bag 130 into a gastric lumen 150. The delivery system 100 comprises an overtube 110, an inner member 140, an outer member 120, a first suture strand 170 looped through a suture bead 160, and a second suture strand 180 looped through the suture bead 160. For purposes of illustrating the delivery system 100, the proximal end of the overtube 110 is not shown in FIG. 1. The intragastric bag 130 is partitioned into bundles 310 (FIG. 3) that are loaded over a surface of the outer member 120, which is shown coaxially slidably disposed over the inner member 140. Generally speaking, the delivery system 100 comprises a pushing mechanism 196 (FIG. 1) that deploys the intragastric bag 130 in a controlled manner by separately advancing each bundle 310 into the gastric lumen 150 to create an implanted assembly 600, as shown in FIG. 6. After bundle 310 is deployed, it is compressed and oriented into a doughnut-shaped bundle 610 as will be described in greater detail below.

Figure 2:
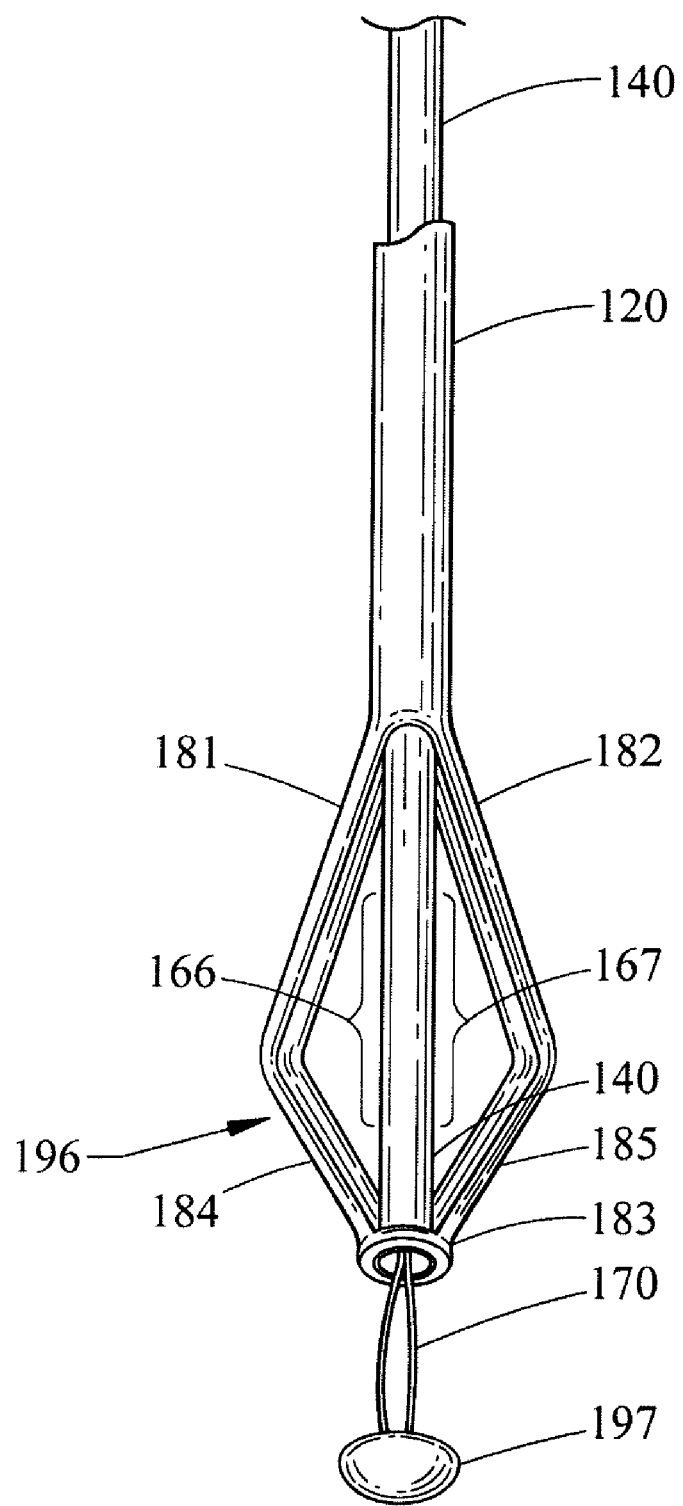
FIG. 2 shows a blown-up view of a pushing mechanism located on the distal end of the delivery system, the pushing mechanism being in a expanded configuration ready to push a bundle into the gastric lumen.

The pushing mechanism 196 advances each of the partitioned bundles 310 by exerting a force in the distal direction against the retaining elements 195 (FIG. 1), as will be discussed in greater detail below. FIG. 2 shows a blown-up view of the pushing mechanism 196. The pushing mechanism 196 comprises segments 181, 182, 184, and 185. The segments 181, 182, 184, and 185 are moveable between an unexpanded configuration (FIG. 7) and an expanded configuration (FIGS. 1 and 2). The segments 181, 182, 184, and 185 may be created by removing strips of material from the outer member 120 at the distal end so as to expose the inner member 140. The distal ends of the outer member 120 and inner member 140 along region 183 are fixedly connected. In the example shown in FIGS. 1, 2, and 7, the distal ends are heat bonded. Other means for affixing the distal ends of inner and outer members 120 and 140 are contemplated and would be appreciated by one of ordinary skill in the art. The remainder of the outer member 120 is slidably disposed over the inner member 140. Proximal movement of the inner member 140 relative to the outer member 120 will cause the segments 181, 182, 184, and 185 to move from an unexpanded configuration (FIG. 7) to an expanded configuration (FIG. 1). Distal movement of the inner member 140 relative to the outer member 120 will cause the segments 181, 182, 184, and 185 to move from an expanded configuration (FIG. 1) to an unexpanded configuration (FIG. 7).

Figure 7:
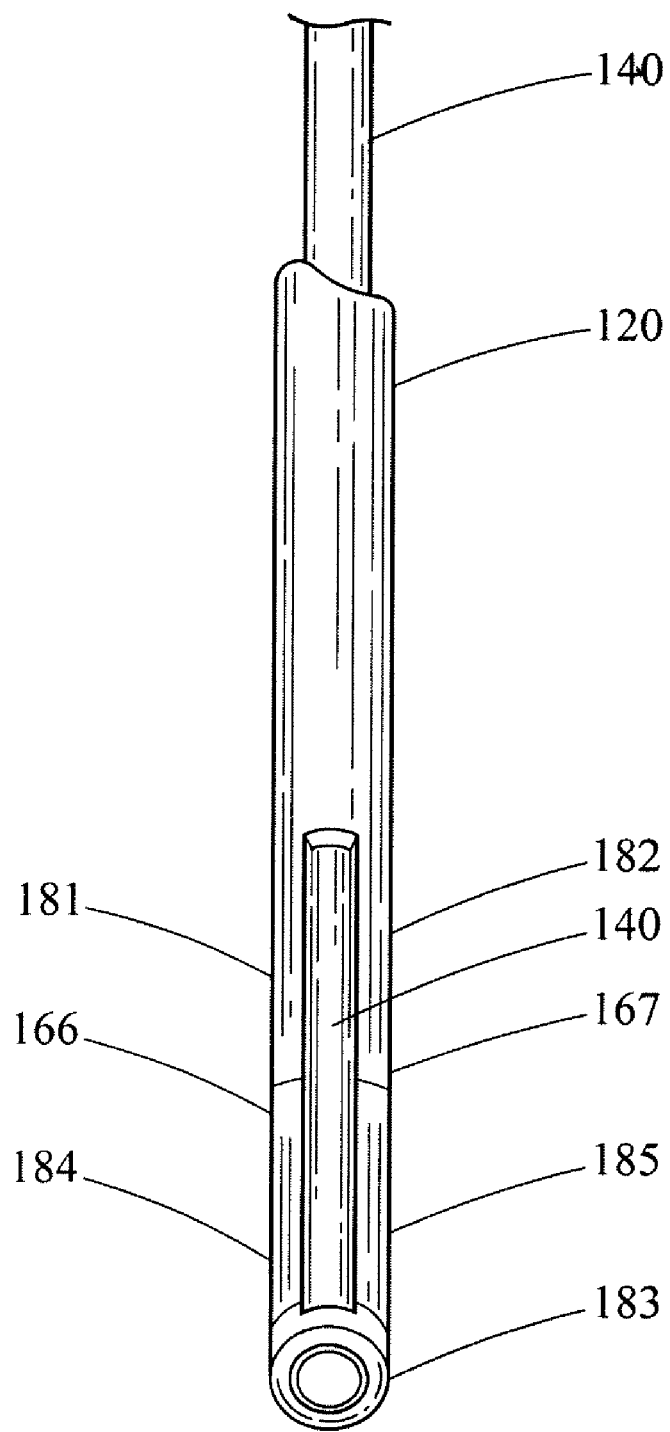
FIG. 7 shows a blown-up view of the pushing mechanism of FIG. 2, the pushing mechanism being in an unexpanded configuration.

The unexpanded configuration has segments 181 and 184 being substantially parallel and adjacent to a first portion 166 of the inner member 140 and segments 182 and 185 being substantially parallel and adjacent to a second portion 167 of the inner member 140 (FIG. 7). The segments 181, 184, and 182, 185 are sufficiently adjacent to their respective first and second portions 166, 167 of the inner member 140 such that the segments 181, 184, and 182, 185 can be retracted under a retaining element 195, as will be explained in greater detail below.

The expanded configuration (FIG. 2) has segments 181 and 184 spaced away from the first portion 166 of the outer member 120 and segments 182 and 185 spaced away from the second portion 167 of the outer member 120 (FIG. 2). The segments 181, 184, and 182, 185 in the expanded configuration span a lateral distance (FIGS. 1 and 2) sufficiently greater than the outer diameter of the retaining element 195 such that the segments 181, 184, and 182, 185 of the pushing mechanism 196 can push against the retaining element 195 of the bundle 310 from within the bag 130 to advance the bundle 310 into the gastric lumen 150.

Other pushing mechanisms are contemplated and would be appreciated by one of ordinary skill in the art. For example, the pushing mechanism 196 may comprise a cannula or the like with stiffening wires which are pre-bent to reliably fold-up when shortened. The pushing mechanism may be biased in the expanded or unexpanded configuration.

The delivery system 100 also includes a first suture strand 170, a second suture strand 180, and a suture bead 160. The first suture strand 170 loops through a distal aperture 163 of the suture bead 160 and the second suture strand 180 loops through a proximal aperture 162 of the suture bead 160. The first suture strand 170 extends distally through the inner member 140 and affixes to distal button 197, which is located within the first deployed bundle 135 (FIG. 1). The first suture strand 170 extends between the proximal button 198 and the distal button 197 and helps to maintain the doughnut-shaped bundle 610 assembly (FIG. 6). FIG. 1 shows the second suture strand 180 pulled proximally back for purposes of visually seeing the components of the delivery system 100. The length of the second suture strand 180 as shown in FIG. 1 remains constant at about 5 inches. In the embodiment of FIG. 6, about 20 collapsed doughnut-shaped bundles 610, may fit onto 5 inches of the second suture strand 180 to achieve proper compression and orientation of the bundles 610 therealong. There is substantially no slack in the second suture strand 180. Loading additional bundles 610 into the gastric lumen 150 would require increasing the length of the second suture strand 189. In the embodiment of FIG. 6, adding 5 more bundles 610 would require about an additional 1 inch of suture strand 610 to achieve proper compression and orientation of all of the bundles 610. It should be understood that the number of bundles 610 that may fit onto the second suture strand 180 may vary and is not intended to be limited in any way to the embodiment described in FIG. 6.

Figure 4:
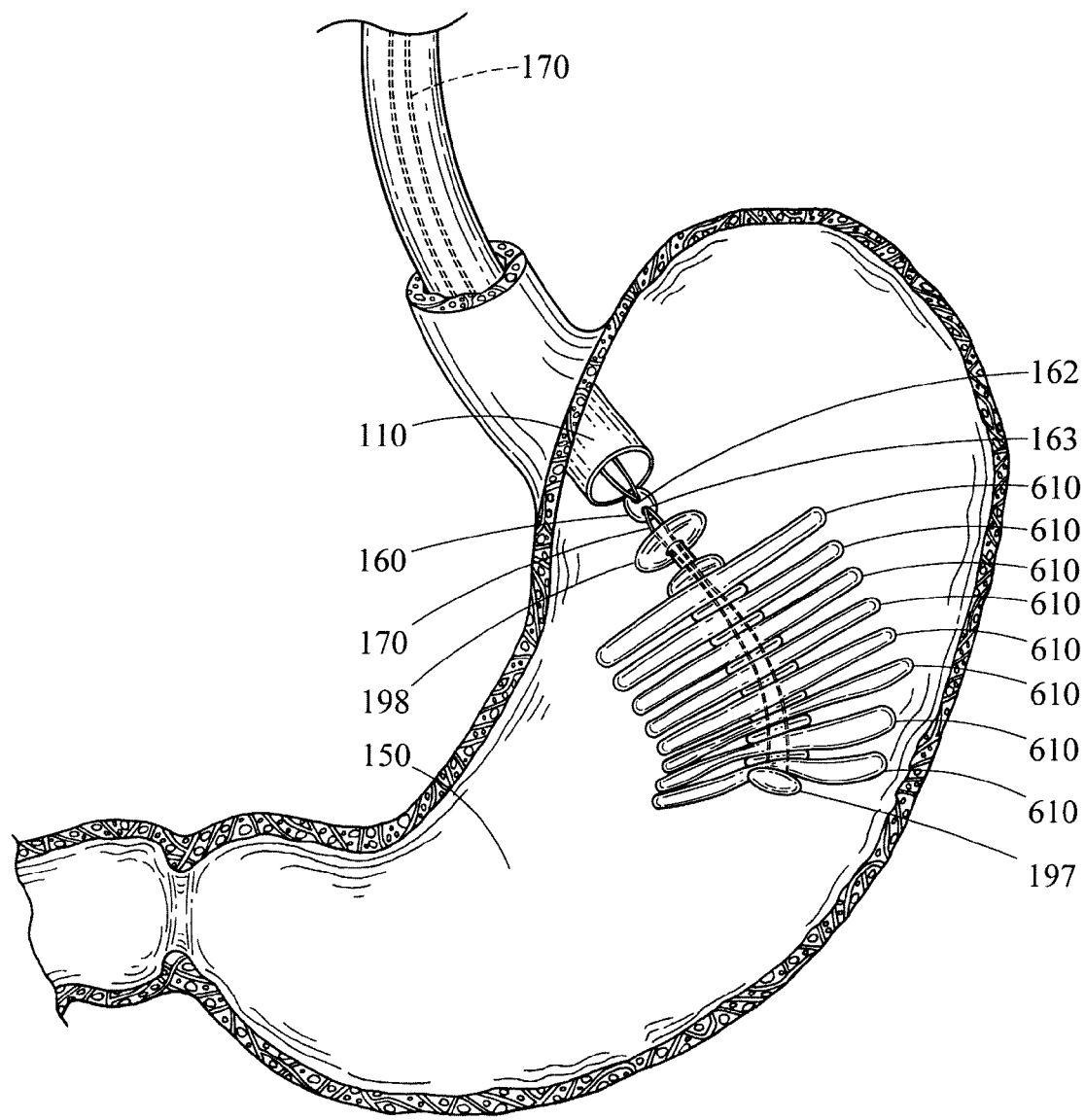
FIG. 4 shows the delivery system of FIG. 1 having deployed bundles but prior to formation of the doughnut-shaped bundle structures.
Figure 5:
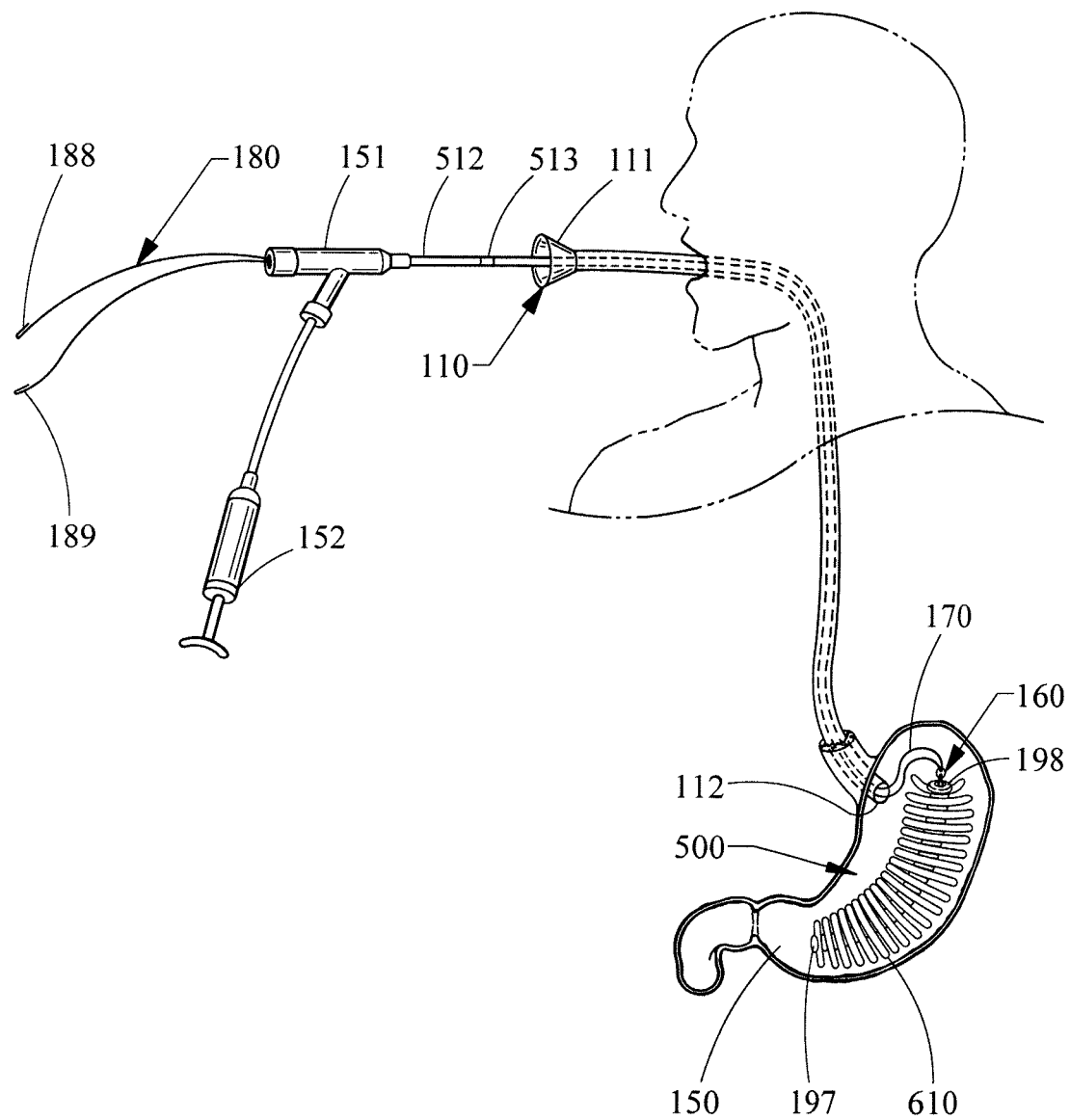
FIG. 5 shows the delivery system of FIG. 1 having deployed all the bundles and formed the doughnut-shaped bundles but prior to securing the bundles with a proximal button.

The second suture strand 180 extends proximally from the overtube 110 and touhy borst adapter 151, terminating as a first free end 188 and a second free end 189 (FIG. 5). The first free end 188 and the second free end 189 of the second suture strand 180 are used primarily during deployment to maintain tension on the deployed bundle 135 (FIG. 1) to enable formation of the preferred doughnut-shaped bundles 610 (FIGS. 4-6), as will be explained in greater detail below. The second suture strand 180 may be removed after complete deployment and formation of all of the doughnut-shaped bundles 610. The suture bead 160, in addition to providing a region through which the first and the second suture strands 170 and 180 may be looped, moves distally along the first suture strand 170 and snaps over the proximal button 198 of the intragastric bag 130 to secure the bag 130 within the lumen after all the bundles 130 have been deployed, as will be explained in greater detail below.

Although the suture bead 160 has been shown having a proximal aperture 162 and a distal aperture 163, the bead may 160 may possess a single aperture through which the first and second suture strands 170, 180 may extend. The suture bead 160 may be formed from any biocompatible material. In one embodiment, the bead 160 may be formed from stainless steel. In another embodiment, the bead 160 may be formed from gold.

The delivery system 100 also includes an overtube 110. Referring to FIG. 5, the overtube 110 includes a proximal end 111, a distal end 112, and a lumen configured to receive the intragastric bag 130 and other devices. The distal end 112 of the overtube 110 is disposed within the gastric lumen 150 during the deployment procedure. The proximal end 111 of the overtube 110 extends outside of the patient. The size of the lumen of the overtube 110 is related to the size of the bundled intragastric bag 130. The overtube 110 is typically configured to extend along the esophagus with its distal end 112 terminating within the vicinity of the lower esophageal sphincter.

Still referring to FIG. 5, the delivery system 100 may also comprise a tuohy borst adapter 151 and a hand pump 152 connected to a side port of the tuohy borst adapter 151. The tuohy borst adapter 151 as shown in FIG. 5 is disposed proximal of the proximal end 111 of the overtube 110. The first free end 188 and the second free end 189 of the second suture strand 180 extend through the tuohy borst adapter 151. The hand pump 152, as will be explained below, inflates the deployed bundles 135 so as to create the collapsed doughnut shaped bundles 610. Other devices may also be connected to the tuohy borst adapter 151.

Figure 3:
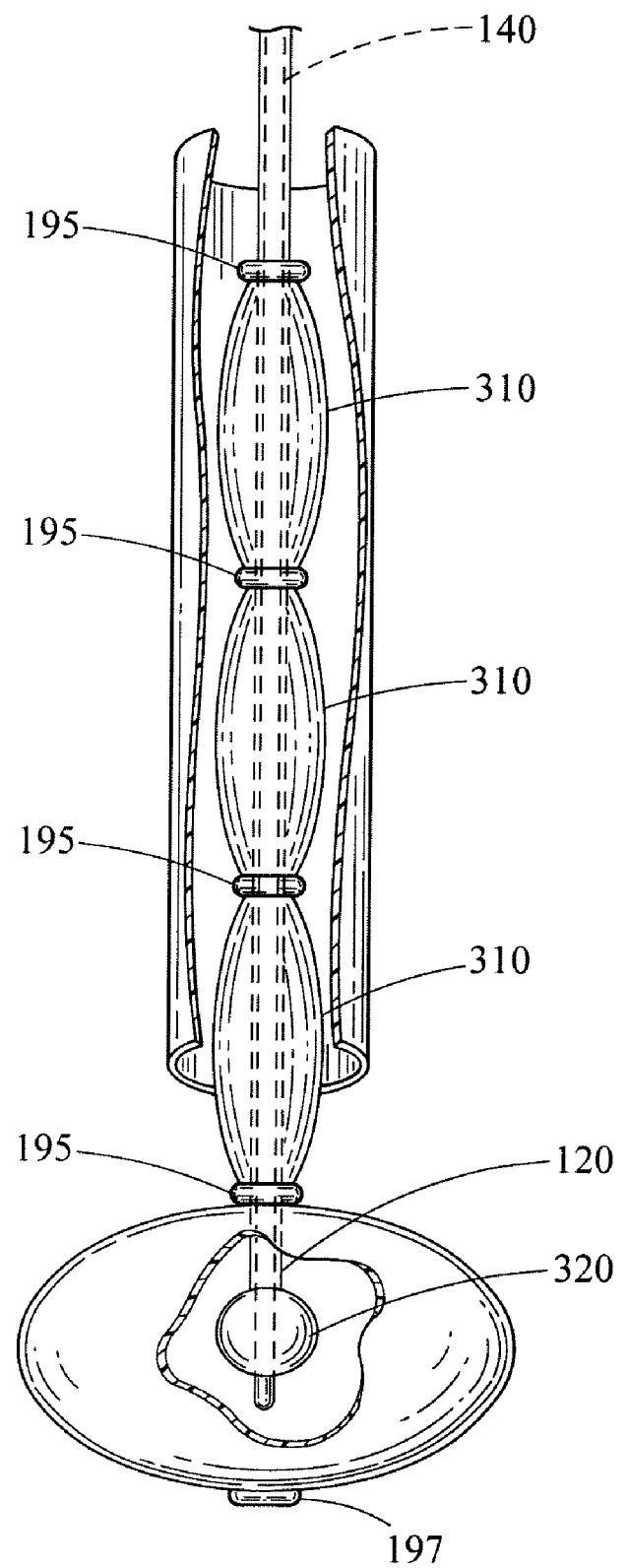
FIG. 3 shows an alternative balloon pushing mechanism.

Having described the components of the delivery system 100, a method of deploying the intragastric bag 130 will now be described with reference to the pushing mechanism 196 that can move between an unexpanded configuration (FIG. 7) and an expanded configuration (FIG. 2). The bag 130 is loaded about the outer member 120 and partitioned into bundles 310. FIG. 3 shows the bundles 310 loaded over the outer member 120. The bundles 310 may be created by positioning retaining elements 195 (e.g., o-rings) circumferentially about the bag 130, as can be clearly seen in FIG. 3. The bag 130 is partitioned into several bundles 310 via retaining elements 195 to facilitate delivery of the bag 130 in a bundle-by-bundle manner. The spacing of the retaining elements 195 may be selectively varied to achieve a predetermined size of the bundles 310. In the example of FIG. 1, the retaining elements 195 are placed about six inches apart from each other. The bundles 310 may span the entire longitudinal length of the outer member 120.

Having loaded the bag 130 onto the outer member 120 and partitioned the bag 130 into bundles 310 (FIG. 3), the pushing mechanism 196 is configured to be unexpanded as shown in FIG. 7. The pushing mechanism 196 in its unexpanded configuration (FIG. 7) within the bag 130 is positioned adjacent to and proximally of the most distal retaining element 195 as shown in FIG. 1. At this juncture, the segments 181, 184 and 182, 185 are expanded outwardly a sufficient amount such that the segments 181, 184 and 182, 185 span a lateral length greater than a diameter of the retaining element 195, as shown in FIG. 1. Proximal movement of the inner member 140 relative to the outer member 120 will cause the segments 181, 182, 184, and 185 to move from an unexpanded configuration (FIG. 7) to an expanded configuration (FIG. 1). With the pushing mechanism 196 in its expanded configuration, the outer member 120 is advanced distally so as to enable the segments 181, 184 and 182, 185 to contact the retaining element 195 and exert a sufficient force on the retaining element 195 in the distal direction. The o-ring 195 is extended sufficiently tight circumferentially about the bag 130 such that it does not move distally along the bundle 130 when incurring a force in the distal direction from the pushing mechanism 196. The force on the o-ring is transmitted to the corresponding bundle 310 of the retaining element 195, thereby causing the bundle 130 (FIG. 1) located distal of the retaining element 195 to be pushed into the gastric lumen 150.

During movement of the pushing mechanism 196 between an unexpanded and expanded configuration, a proximal marker 512 (FIG. 5) may be used to visually monitor how far to retract the unexpanded pusher mechanism 196. A distal marker 513 (FIG. 5) may also be used to visually monitor how far to advance the expanded pusher mechanism 196.

After bundle 310 is deployed, it is compressed and oriented into a doughnut-shaped bundle 610 as will now be described. The deployed bundle 135 (FIG. 1) may be inflated with air using a hand pump 152, which is connected to the tuohy borst adapter 151 (FIG. 5). Pressurized air enters into the tuohy borst adapter 151 and travels distally along the outer member 120 until it enters the deployed bundle 135. Introduction of air by hand pump 152 (FIG. 5) into deployed bundle 135 causes the deployed bundle 135 to inflate, as shown in FIG. 1. The second suture strand 180 is used to exert tension on the deployed bundles 135 so as to collapse each of the deployed bundles 135 into disc-shape or doughnut-shape bundles 610. In particular, the free ends 188 and 189 of the second suture strand 180 are pulled proximally through the tuohy borst adapter 151. Because the second suture strand 180 is connected to the first suture strand 170 by suture bead 160, pulling of the free ends 188 and 189 of the second suture strand 180 causes the first suture strand 170 to be pulled proximally. Because the first suture strand 170 extends distally along the entire delivery system 100 and is affixed at the distal button 197, the pulling of the first suture strand 170 causes the inflated deployed bundle 135 to collapse so as to remove a substantial portion of the air within the inflated bundle 135. The doughnut-shaped bundle 610 (FIGS. 4-6) forms. Configuring the bundles 135 into doughnut-shape bundles 610 allows adequate compression of the deployed bundles 610 and proper orientation so as to allow all of the bundles 610 to fit onto the finite length of the first suture strand 170. In this example, the intragastric bag 130 has a longitudinal length of about 6 feet in its uncompressed and unpartitioned state. Configuring an assembly of doughnut-shaped bundles 610 enables such a large amount of material to fit onto the first suture strand 170, which has a final implanted length of about 6 inches as shown in FIG. 6.

During deployment of the bundles and formation of the doughnut shaped bundles 610, the positioning of the suture bead 160 is visually monitored to ensure that it is positioned proximal of the mark 199 (FIG. 1). Such positioning of the suture bead 160 allows adequate and proper compression of the deployed bundles 610 and ensures that the suture bead 160 does not get intertwined with one of the bundles 130 loaded on the outer member 120. Pulling of the free ends 188 and 189 of the second suture strand 180 enables tension to be maintained on the bundles 130 as they are each being pushed by pushing mechanism 196 into the gastric lumen 150. The overtube 110 at this stage creates sufficient counter-traction to prevent the bundles 610 from sliding back into the overtube 110, thereby maintaining the doughnut-shaped bundle 610 in its implanted position within the gastric lumen 150.

Having deployed the distal-most first bundle 135 and formed it into a doughnut-shaped bundle 610, the next-most distal bundle 310 is ready to be deployed. In order to position the pushing mechanism 196 proximal and adjacent to the retaining element 195 associated with the next-most distal bundle 310 to be deployed, the segments 181, 184 and 182, 185 of the pushing mechanism 196 are unexpanded (FIG. 7) so as to enable the pushing mechanism 196 to attain a low profile that can be pulled underneath the retaining element 195. This orientation is achieved by distally moving the inner member 140 relative to the outer member 120 to allow segments 181, 182, 184, and 185 to move from an expanded configuration (FIG. 1) to an unexpanded configuration (FIG. 7).

The bundles 130 remain in position along the outer member 120 during retraction of the unexpanded pushing mechanism. After unflaring the pushing mechanism 196, it is retracted proximally until it is disposed proximal and adjacent to the next proximally disposed retaining element 195. The proximal marker 512 helps to visually monitor how far to proximally retract the pushing mechanism 196. With the pushing mechanism 196 in such a position, it can be expanded so as to push retaining element 195 and push the next-most distal bundle 310 into the gastric lumen 150. Introduction of air with the hand pump 152 enables air to inflate this deployed second bundle 135. The previously deployed retaining element 195 (i.e., the distal-most retaining element) sufficiently squeezes around the material of the bag 130 such that the air does not flow into the first distal-most bundle that has been deployed. The free ends 188 and 189 of the first suture strand 180 are pulled to collapse the deployed second bundle 135 and form the second doughnut-shaped bundle 610.

The above procedure is repeated until all of the bundles 310 that are loaded onto the outer member 120 have been deployed into the gastric lumen 150 and thereafter properly compressed and oriented into the doughnut-shaped bundles 610. As subsequent bundles 310 are pushed into the gastric lumen 150, the implanted assembly 500 (FIG. 5) becomes increasingly compressed. FIG. 4 shows that all of the bundles 130 have been deployed from the outer member 120, but prior to forming the collapsed doughnut-shaped bundles 610. FIG. 5 shows that bundles 130 have been deployed into the gastric lumen 150 and thereafter properly compressed and oriented into the doughnut-shaped bundles 610. A distal button 197 helps to maintain the configuration of the bundles 610 at the distal end. The distal button 197 may be formed from the same material as the bag 130.

Having deployed all of the bundles 130 from the outer member 120, the outer member 120 and inner member 140 may be removed from the overtube 110 while simultaneously holding the second suture strand 180 tight. The tuohy borst adapter 151 is opened to allow pulling back of the inner and outer member 140, 120 over the suture strands 170 and 180 and out of the overtube 110.

At this juncture, the suture bead 160 may be secured to the proximal button 198, which is affixed to the most proximal deployed doughnut-shaped bundle 610 at proximal end 607 (FIG. 6). FIG. 4 shows that the suture bead 160 is introduced through the overtube 110 by threading it over the first suture strand 170. A pushing member may be introduced proximally of the suture bead 160 to distally push the suture bead 160 towards the proximal button 198 at proximal end 607 until the suture bead 160 snaps over the proximal button 198 (FIG. 6).

Having secured the suture bead 160 onto the proximal button 198, the implanted device 500 is secured in position between proximal button 198 and distal button 197 as shown in FIG. 5. One of the free ends 188 and 189 of the second suture strand 180 may be pulled to remove the suture strand 180 from the proximal aperture 162 of the suture bead 160. Having removed the second suture strand 180, the overtube 110 may also be withdrawn.

Although the above deployment procedure has been described using a pushing mechanism 196 comprising the flaring and unflaring of segments 181, 184 and 182, 185, alternative pushing mechanisms are contemplated. For example, FIG. 3 shows an expandable balloon 320 that may be used to push the bundles 310 from the outer member 120 into the gastric lumen 150. Similar, to the flaring and unflaring of the pushing mechanism 196, the balloon 320 is adapted to be configured from a decreasing diameter to an increasing diameter. The balloon 320 is shown disposed along the distal end of the outer member 120. Similar to the flaring and unflaring described with respect to the pushing mechanism 196 in FIGS. 2 and 7, respectively, the balloon 320 pushes a retaining element 195 and its corresponding bundle 310 by flaring or inflating in size so as to create an expanded configuration that is sufficient to contact and push the retaining element 195 and its corresponding bundle 320 in a distal direction into the gastric lumen 150. The use of distal marker 513 (FIG. 5) may help to determine how far to push the inflated balloon 320 in order to sufficiently deploy the bundle 310. Subsequently, the balloon 320 is sufficiently unexpanded or deflated such that it can pass underneath the retaining element 195. The use of proximal marker 512 (FIG. 5) may help to determine how far to retract the deflated balloon 320 in order to position the balloon 320 proximal to and adjacent the next-most distal retaining element 195 and its corresponding bundle 320 to be deployed.

The doughnut-shaped bundles 610 of the final implanted assembly 600 may contain relatively minimal air. After inflation of air into the bundles 610 and pulling of the second suture strand 170 to create the compressed doughnut-shaped orientation, a substantial portion of the air may escape through the proximal aperture 162 and distal aperture 163 of the suture bead 160 as well as at the tuohy borst adapter 151. Vacuum may be pulled on the final implanted assembly 600. The vacuum may remove residual air so as to enable more bundles 610 to be deployed.

FIG. 6 shows the final implanted assembly 600 of the deployed bundles 610. The assembly 600 is designed to displace volume within the gastric lumen 150. The assembly 600 in its final implanted state provides a feeling of fullness upon engaging the lumen of the patient, i.e., the stomach walls of the patient. The second suture strand 170 extends between the proximal button 198 and distal button 197 to maintain the bundle-like structure of the assembly 600. The doughnut-shaped bundles 610 are sufficiently sized to substantially prevent migration through the pylorus 155 and the duodenum 156. Although sufficiently sized, the bundles 610 do not possess the long radial folds typically associated with other obesity devices, in which the folds are substantially unconstrained and free to move. In other words, the radial distance from the central axis of the bundle-like structure 610 to the edge of one of the bundles 610 is relatively less as compared to obesity devices partitioned into strips with sharp edges. As a result, there may be fewer tendencies for the material between adjacent bundles 610 to freely move around and irritate the walls of the gastric lumen 150. Additionally, the elimination of the large folds in the radial direction may substantially prevent the folds from being forced to go forward through the duodenum 156 (FIG. 6) due to peristalsis.

Additionally, the doughnut-shaped bundles 610 are relatively atramautic compared to prior intragastric bag implants that possessed sharper edges. As FIG. 6 show, the edges of each of the doughnut-shaped bundles 610 are rounded rather than pointed. The elimination of the pointed edges of the bundles 610 may substantially reduce the chances of stomach irritation which could potentially lead to ulcers.

Another advantage of the assembly 600 is that a lesser number of passes of the bag 130 is required to deploy a larger number of bundles 310. Delivery of the intragastric bag 130 when not compacted and partitioned into a series of bundles may be as long as six feet in longitudinal length. Such a large longitudinal length occupies a large amount of volume and therefore increases the amount of procedure time necessary for the delivery system 100 to fully deploy the bag 130. Because the bundle-like structures 130 (FIG. 3) create a dense configuration, less passes of the material is required as compared to other non-bundled obesity devices to deploy a relatively large number of bundles.

The bundles 610 of the implanted assembly 600 may be formed from any biocompatible material that can withstand the acidic environment of the gastric lumen 150, including, but not limited to, plastic, nylon, polyesters, polyurethanes, polyethylenes (e.g., high-density polyethylene, low-density polyethylene), polyamides, fluorinated ethylene propylene and ethylene vinyl acetate copolymer. The bundles 610 may be formed from a complaint or non-compliant polymeric material.

The implanted assembly 600 may be removed after a predetermined period of time when sufficient weight loss has occurred. A wire guide may be inserted into the gastric lumen 150, and the overtube 110 may be loaded over the wire guide. With the overtube 110 positioned at about the lower esophageal sphincter, a cutting element such as scissors may be deployed through the lumen of the overtube 110. Upon reaching the proximal button 198, the cutting element cuts the second suture strand 170 which is captured inside the proximal button 198. Forceps are thereafter introduced through the overtube 110 to grasp the proximal button 198 and withdraw the button 198 through the lumen of the overtube 110. A snare may subsequently be introduced to capture the proximal end 607 of the assembly 600 and pull the bundles 610 out of the overtube 110.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention.

The invention claimed is:

1. A delivery system for introducing an obesity device into a gastric lumen, comprising:
    an overtube including a proximal end and a distal end;
    an inner member having a first distal end;
    an outer member including a second distal end, the outer member slidably disposed over the inner member, the outer member comprising a pushing mechanism disposed at the second distal end, the pushing mechanism moveable between an expanded configuration and an unexpanded configuration, wherein the pushing mechanism in the expanded configuration is adapted to push an incremental length of the obesity device into the gastric lumen; and
    an intragastric bag disposed over the outer member, the intragastric bag comprising a plurality of bundles formed by a plurality of retaining elements,
    wherein the pushing mechanism comprises a plurality of segments disposed about the second distal end of the outer member, the second distal end of the outer member being fixedly connected to the first distal end of the inner member, and
    wherein each of the plurality of segments in the expanded configuration span a lateral length greater than a diameter of each of the plurality of retaining elements.

2. The delivery system of claim 1, further comprising a first suture strand looped through a suture bead and extending to a distal button of the device, the first suture strand being affixed to the distal button disposed at a distal end of the obesity device; and
    a second suture strand looped through the suture bead and proximally extending along the inner member, the second suture strand terminating at a first free end and a second free end at a proximal end of the inner member.

3. The delivery system of claim 1, wherein the first and the second distal ends are fixedly connected by a heat bond.

4. The delivery system of claim 1, wherein the plurality of retaining elements are disposed circumferentially about the intragastric bag at spaced apart locations.

5. The delivery system of claim 4, wherein the plurality of retaining elements comprises o-ring elements.

6. The delivery system of claim 5, wherein the outer member comprises a plurality of markings, wherein the plurality of markings help to visually determine the incremental length that the plurality of bundles are pushed into the gastric lumen, and further wherein the plurality of markings help to visually determine the incremental length that the pushing mechanism in the unexpanded configuration is being retracted.

7. The delivery system of claim 5, further comprising an air pump connected to a tuohy borst adaptor for injecting air into each of the plurality of bundles.

8. The delivery system of claim 1, wherein the intragastric bag comprises a digestive-resistant material in a configuration sufficiently large to prevent the intragastric bag from passing through a mammal's pylorus, wherein the intragastric bag is configured to function as an artificial bezoar, and further wherein the bag comprises a plurality of doughnut-shaped bundles, each of the plurality of doughnut-shaped bundles having atramautic rounded edges.

9. The delivery system of claim 8, wherein each of the plurality of doughnut shaped bundles is interconnected by a suture strand, the suture strand being affixed to a proximal button and a distal button.

10. The delivery system of claim 9, wherein the proximal button is secured to a suture bead.

11. The delivery system of claim 9, each of the plurality of doughnut-shaped bundles being stacked against each other in a direction substantially perpendicular to the suture strand.

12. The delivery system of claim 8, wherein each of the plurality of the doughnut-shaped bundles comprises a flattened disc-shaped bundle.

13. The delivery system of claim 8, wherein each of the plurality of doughnut-shaped bundles is inflatable and compressible.

14. A method for introducing an intragastric bag into a gastric lumen, comprising the steps of:
(a) providing a delivery system comprising:
an overtube including a proximal end and a distal end;
an inner member having a first distal end;
an outer member including a second distal end, the outer member slidably disposed over the inner member, the outer member comprising a pushing mechanism disposed at the second distal end, the pushing mechanism moveable between a expanded configuration and an unexpanded configuration; wherein the pushing mechanism in the expanded configuration spans a distance sufficient to push an incremental length of the bag into the gastric lumen;
(b) partitioning the intragastric bag into a plurality of bundles with a plurality of retaining elements, the plurality of retaining elements being disposed circumferentially about the plurality of bundles, the plurality of retaining elements being spaced apart a predetermined distance from each other;
(c) loading the intragastric bag over the outer member;
(d) proximally pulling the outer member through a first retaining element from the plurality of retaining elements with the pushing mechanism being configured in the unexpanded configuration and positioned in the bag proximal and adjacent to the first retaining element;
(e) expanding the pushing mechanism;
(f) moving the outer member in a distal direction so as to push the first retaining element from the plurality of retaining elements and a first bundle of the plurality of bundles into the gastric lumen.

15. The method of claim 14, further comprising the steps of:
(g) unexpanding the pushing mechanism; and
(h) proximally pulling the outer member through a second retaining element from the plurality of retaining elements such that the pushing mechanism is configured in the unexpanded configuration and positioned in the bag proximal and adjacent to the second retaining element from the plurality of retaining elements;
(i) expanding the pushing mechanism;
(j) moving the outer member in a distal direction; and
(k) pushing the second retaining element from the plurality of retaining elements so as to push a second bundle of the plurality of bundles into the gastric lumen.

16. The method of claim 14, wherein step (d) further comprises visually monitoring a location of a first marker located about the outer member to determine how far to proximally pull back the outer member.

17. The method of claim 14, wherein step (f) further comprises visually monitoring a location of a second marker located about the outer member to determine how far to distally push the outer member.

18. The method of claim 14, further comprising the steps of:
(g) providing a first suture strand looped through a suture bead and extending to a distal button of the device, the first suture strand being affixed to the distal button disposed at a distal end of the bag; and
a second suture strand looped through the suture bead and proximally extending along the inner member, the second suture strand terminating at a first end and a second free end at a proximal end of the inner member;
(h) injecting air into the first bundle; and
(i) pulling the first and the second free ends of the second suture strand such that the first bundle forms a first collapsed doughnut-shaped configuration within the gastric lumen.

19. The method of claim 18, further comprising the step of:
(i) withdrawing the outer member;
(j) threading the first suture strand through a proximal button; and
(k) snapping the proximal button to the suture bead.

20. The method of claim 19, further comprising the steps of:
(I) incising the first and the second free ends of the second suture strand from the proximal button; and
(m) removing the second suture strand.

21. The method of claim 14, further comprising the steps of:
(I) providing a first suture strand looped through a suture bead and extending to a distal button of the device, the first suture strand being affixed to the distal button disposed at a distal end of the bag; and
a second suture strand looped through the suture bead and proximally extending along the inner member, the second suture strand terminating at a first end and a second free end at a proximal end of the inner member;
(m) injecting air into a second bundle; and
(n) pulling the first and the second free ends of the second suture strand such that the second bundle forms a second collapsed doughnut-shaped configuration within the gastric lumen, the second bundle being adjacent to the first bundle.

* * * * *

UNITED STATES PATENT AND TRADEMARK OFFICE
CERTIFICATE OF CORRECTION

| | | |
|---|---|---|
| PATENT NO. | : 8,016,851 B2 | Page 1 of 1 |
| APPLICATION NO. | : 11/965531 | |
| DATED | : September 13, 2011 | |
| INVENTOR(S) | : Travis E. Dillon et al. | |

It is certified that error appears in the above-identified patent and that said Letters Patent is hereby corrected as shown below:

In the Claims

In column 12, claim 18, line 7, before "providing a first" replace "(g)" with --(l)--.

In column 12, claim 18, line 16, before "injecting air into" replace "(h)" with --(m)--.

In column 12, claim 18, line 17, before "pulling the first" replace "(i)" with --(n)--.

In column 12, claim 19, line 22, before "withdrawing the outer" replace "(i)" with --(o)--.

In column 12, claim 19, line 23, before "threading the first" replace "(j)" with --(p)--.

In column 12, claim 19, line 25, before "snapping the proximal" replace "(k)" with --(q)--.

In column 12, claim 20, line 28, before "incising the first" replace "(l)" with --(r)--.

In column 12, claim 20, line 30, before "removing the second" replace "(m)" with --(s)--.

In column 12, claim 21, line 33, before "providing a first suture" replace "(l)" with --(t)--.

In column 12, claim 21, line 42, before "injecting air into" replace "(m)" with --(u)--.

In column 12, claim 21, line 43, before "pulling the first and the" replace "(n)" with --(v)--.

Signed and Sealed this
Thirty-first Day of January, 2012

David J. Kappos
*Director of the United States Patent and Trademark Office*